(12) United States Patent
Haisch

(10) Patent No.: US 7,110,173 B2
(45) Date of Patent: Sep. 19, 2006

(54) MICROSCOPY SYSTEM AND METHOD

(75) Inventor: Michael Haisch, Aalen (DE)

(73) Assignee: Carl Zeiss AG, Oberkochen (DE)

( * ) Notice: Subject to any disclaimer, the term of this patent is extended or adjusted under 35 U.S.C. 154(b) by 55 days.

(21) Appl. No.: 10/991,756

(22) Filed: Nov. 18, 2004

(65) Prior Publication Data

US 2005/0117207 A1    Jun. 2, 2005

(30) Foreign Application Priority Data

Nov. 19, 2003  (DE) ............................... 103 53 961

(51) Int. Cl.
*G02B 21/00* (2006.01)
(52) U.S. Cl. .................... 359/384; 248/124.1
(58) Field of Classification Search ................ 359/368, 359/384; 248/123.11, 123.2, 124.1
See application file for complete search history.

(56) References Cited

U.S. PATENT DOCUMENTS

| 3,887,267 A | 6/1975 | Heller |
| 4,516,840 A | 5/1985 | Nakahashi et al. |
| 5,345,334 A | 9/1994 | Heller |
| 5,748,366 A * | 5/1998 | Yasunaga et al. ........... 359/368 |
| 5,835,266 A * | 11/1998 | Kitajima ..................... 359/384 |
| 2004/0036962 A1 | 2/2004 | Brunner et al. |

FOREIGN PATENT DOCUMENTS

| DE | 41 33 241 A1 | 4/1993 |
| DE | 102 03 215 A1 | 8/2003 |

* cited by examiner

*Primary Examiner*—Mark A. Robinson
(74) *Attorney, Agent, or Firm*—Potomac Patent Group PLLC

(57) ABSTRACT

A microscopy system comprises a microscopy optics and a stand supporting the microscopy optics. The stand has a plurality of hinges, of which a first group comprises a position detecting sensor for sensing a hinge position and a second group comprising an actuator for the change of the hinge position. In an automatic control mode, the actuators are controlled in dependence of signals of the position detecting sensors.

9 Claims, 3 Drawing Sheets

MICROSCOPY SYSTEM AND METHOD

BACKGROUND OF THE INVENTION

1. Field of the Invention

The invention relates to a microscopy system and in particular to a surgical microscopy system comprising a microscopy optics and a stand for carrying the microscopy optics. The invention further relates to a method of controlling a microscopy system.

2. Brief Description of the Related Art

A microscopy optics generally comprises an objective lens having an optical axis and an object plane in which an object to be observed is to be disposed. The microscopy optics is configured to image a region of the object being located in a focus region of the microscopy optics.

A stand of a conventional microscopy system comprises a plurality of stand members comprising a base stand member and an objective lens supporting stand member supporting the objective lens. Pairs of stand members are connected to each other by respective such that the hinges of each pair may be displaced relative to each other. For example, the hinge members of the pair may be tilted or swiveled relative to each other. By operating the hinges, i.e. by displacing relative to each other the stand members which are connected with each other by the hinges, it is possible, on the one hand, to displace the focus region of the microscopy optics towards a desired region of the object of interest, and, on the other hand, to orientate an optical axis of the objective lens such that the desired region of the object is imaged by the microscopy optics from a desired point of view or under a desired viewing angle.

The stand of a conventional microscopy system may comprise a group of hinges allowing a user, in at least one operation mode, to substantially freely displace relative to each other the stand members connected to each other by the hinges of that group by applying a force to a component of the microscopy system. The force may be applied to a component such as a stand member or the microscopy optics or any other component provided on the microscopy optics, such as a handle bar or other. The stand members are substantially freely displaceable relative to each other in that sense that only a low force to overcome such as a remaining frictional force of the respective hinges has to be applied to achieve the desired displacement of the microscopy optics.

To this end, the members of the stand may be balanced such that a gravitational force applied to the stand members and the microscopy optics will substantially not provoke any displacement of the microscopy optics.

The hinges which are substantially free displaceable in this operation mode may be further provided with a brake in order to block an accidental displacement of the microscopy optics in another mode of operation.

The conventional microscopy system may further comprise another group of hinges including an actuator to change the relative positions of the stand members which are connected with each other by the respective hinge of this group. These actuators may be controlled by the user by, for example, a switch or the like. Controlling the actuators may result, for example, in a change of the orientation of the optical axis of the objective lens.

If the user wants to observe a region of the object being observed from a different point of view or under a different viewing angle, he will grasp the stand or a component of the microscopy optics with his hand in order to displace the objective lens to a desired new position. Due to the displacement of the objective lens, the focus region of the microscopy optics and the region of interest of the object will no longer coincide, and the user finally has to reorientate and, if necessary, also to displace the optical axis of the objective lens by controlling the respective actuators such that the region of interest of the object again coincides with the focus region of the microscopy optics. This procedure is cumbersome and results in that the user, even if the observation of the object under a different perspective appears desirable, either does not perform such observation or requires a long time for performing the necessary steps.

SUMMARY OF THE INVENTION

In view of the above, it is an object of the present invention to provide a microscopy system and a method for the controlling a microscopy system having improved possibilities of changing a desired point of view or viewing angle.

In order to achieve the above object, the invention provides a microscopy system and method in which some pairs of hinged stand members are substantially free displaceable relative to each other and some other pairs of hinged stand members are displaceable relative to each other under control of an actuator associated with the respective hinge, wherein the actuator is controlled based on a position signal of a position detection system of the microscopy system.

According to an embodiment of the invention, a microscopy system for displaying an image of an object to be examined comprises: a microscopy optics for imaging the object, the microscopy optics comprising at least one objective lens having an optical axis, an object plane and a focus region in which the object to be imaged is to be disposed, wherein the optical axis intersects with the object plane within the focus region; and a stand comprising a plurality of stand members, a first hinge group having at least one first hinge and a second hinge group having at least one second hinge, each hinge of the first and second hinge groups connecting a pair of stand members such that the stand members connected by the respective hinge may be displaced relative to each other, the plurality of stand members comprising a base stand member and an objective lens supporting stand member supporting the at least one objective lens; the at least one first hinge of the first hinge group allowing, in at least a first mode of operation of the microscopy system, a user to freely displace relative to each other the two stand members hinged together by the first hinge by applying a force to the stand; the at least one second hinge of the second hinge group comprising a first actuator for displacing relative to each other the two stand members hinged together by the second hinge; the system further comprising: a position detecting system having at least one sensor, wherein the position detecting system is configured to generate a position signal representing a change of a position of the at least one objective lens based on a sensor signal of the at least one sensor; and a controller, configured to actuate, in the first mode of operation of the microscopy system, the first actuator of the at least one second hinge to displace the pair of stand members connected by the at least one second hinge based upon the position signal generated by the position detecting system.

According to an embodiment of the invention, the position detection system comprises position sensors attached to hinges of a first group of those hinges, which are substantially free displaceable for the displacement of the objective lens.

According to an embodiment of the invention, the microscopy system comprises a controller in order to control an actuator of a hinge of a second hinge group of hinges based upon the position signal.

According to an exemplary embodiment, the control of the actuator is carried out such that a displacement of the focus region of the microscopy optics in the coordinate system is less than a displacement being affected by applying of a force to the stand or parts of the microscopy optics. Thus, the displacement of the focus region in the coordinate system may be less than 30% of the displacement of the objective lens in the coordinate system. According to other exemplary embodiments, the displacement of the focus region in the coordinate system may be less than 20%, less than 10% or even less than 5% of the displacement of the objective lens in the coordinate system.

Herewith, a required effort to again let the focus region of the microscopy optics coincide with the interesting region of the object after a displacement of the microscopy optics can be considerably reduced. Preferably, it is possible that the focus region of the microscopy optics remains at a same position in the coordinate system even after displacement of the latter. Changes of the point of view or viewing angle for observation are relatively easy to be obtained, accordingly.

According to an exemplary embodiment, the objective lens is an objective lens having a working distance which may be changed in order to change a distance between the focus region and the objective lens.

According to an exemplary embodiment, the change of the working distance is also based upon the position signal. According to an alternative embodiment, the microscopy optics can comprise an auto-focus system in order to measure a distance between the objective lens and the observed object and to adjust the working distance such that the focus region coincides with the interesting region of the observed object.

According to a further exemplary embodiment, the microscopy system comprises a mouth switch being firmly connected with the objective lens. The mouth switch may be actuated by a mouth of the user while looking into oculars of the microscopy optics. By this, the user can release brakes which block the relative displacement of the hinges of the first group of hinges when the mouth switch is not actuated and is able to apply a necessary force for the displacing of these hinges also via the mouth switch onto the objective lens and thus onto the stand.

BRIEF DESCRIPTION OF THE DRAWINGS

In the following, exemplary embodiments of the present invention are explained in further details with reference to the figures, wherein.

DETAILED DESCRIPTION

Figure 1:
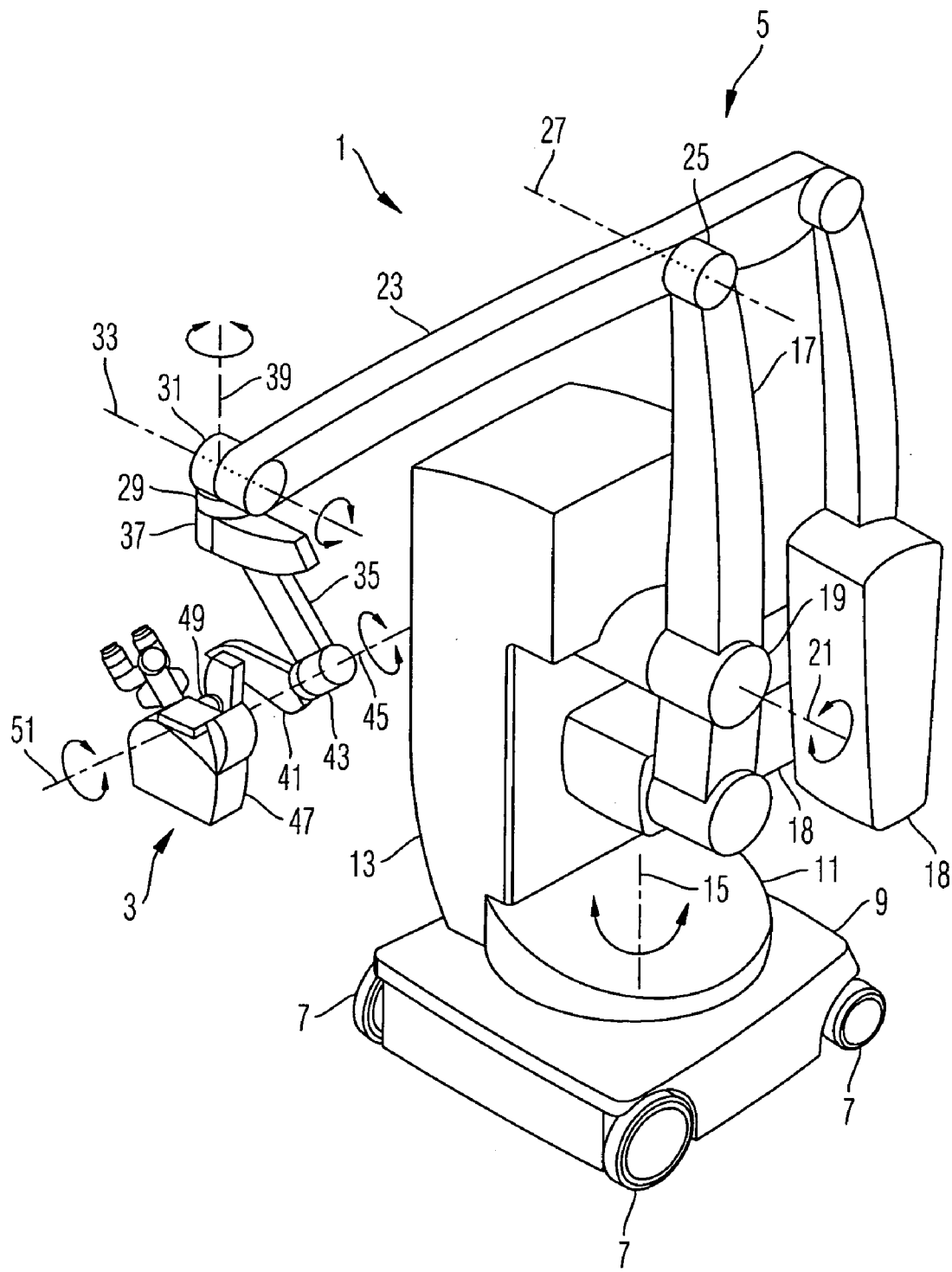
FIG. 1 is an illustrative perspective schematic view of a microscopy system according to an embodiment of the invention.

In the exemplary embodiments described below, components that are similar in function and structure are designated as far as possible by similar reference numerals. Therefore, to understand the features of the individual components of a specific embodiment, the descriptions of other embodiments and of the summary of the invention should be referred to.

FIG. 1 shows a schematic perspective view of a microscopy system 1 comprising a microscopy optics 3, mounted on and carried by a stand 5. The stand 5 comprises, as a base stand member, a pedestal 9 having wheels. The base stand member 9 supports a further stand member 13 via a pivot hinge 11 being ratable about a vertically extending pivot axis 15. A further stand member 17 is displaceably supported on the stand member 13 via a hinge 19 having a horizontal pivot axis 21. Again, at stand member 17, a further stand member 23 is displaceably supported via a hinge 25 about a horizontal pivot axis 27. Again, at stand member 23, a further stand member 29 is displaceable supported via a hinge 31 around a horizontal pivot axis 33. Again, the stand member 29 supports a stand member 35 being displaceable via a hinge 37 around a pivot axis 39. Again, at the stand member 35, a further stand member 41 is, via a hinge 43, displaceable hinged around a pivot axis 45, and, finally, a chassis 47 of the microscope is displaceably hinged via a hinge 49 around a pivot axis 51 to the stand member 41. By this, the microscope 3 can be displaced within a useful working volume and can be oriented by displacing the stand members around the pivot axes.

Two counter-balances 18 of the stand 5 are configured to balance the microscope 3 with respect to the pivot axes 21 and 27, and the user only needs to overcome a remaining friction force in order to displace the stand around these axes. Also for displacing the stand around the vertically oriented pivot axis 15, the user only needs to overcome a remaining friction force.

Figure 2:
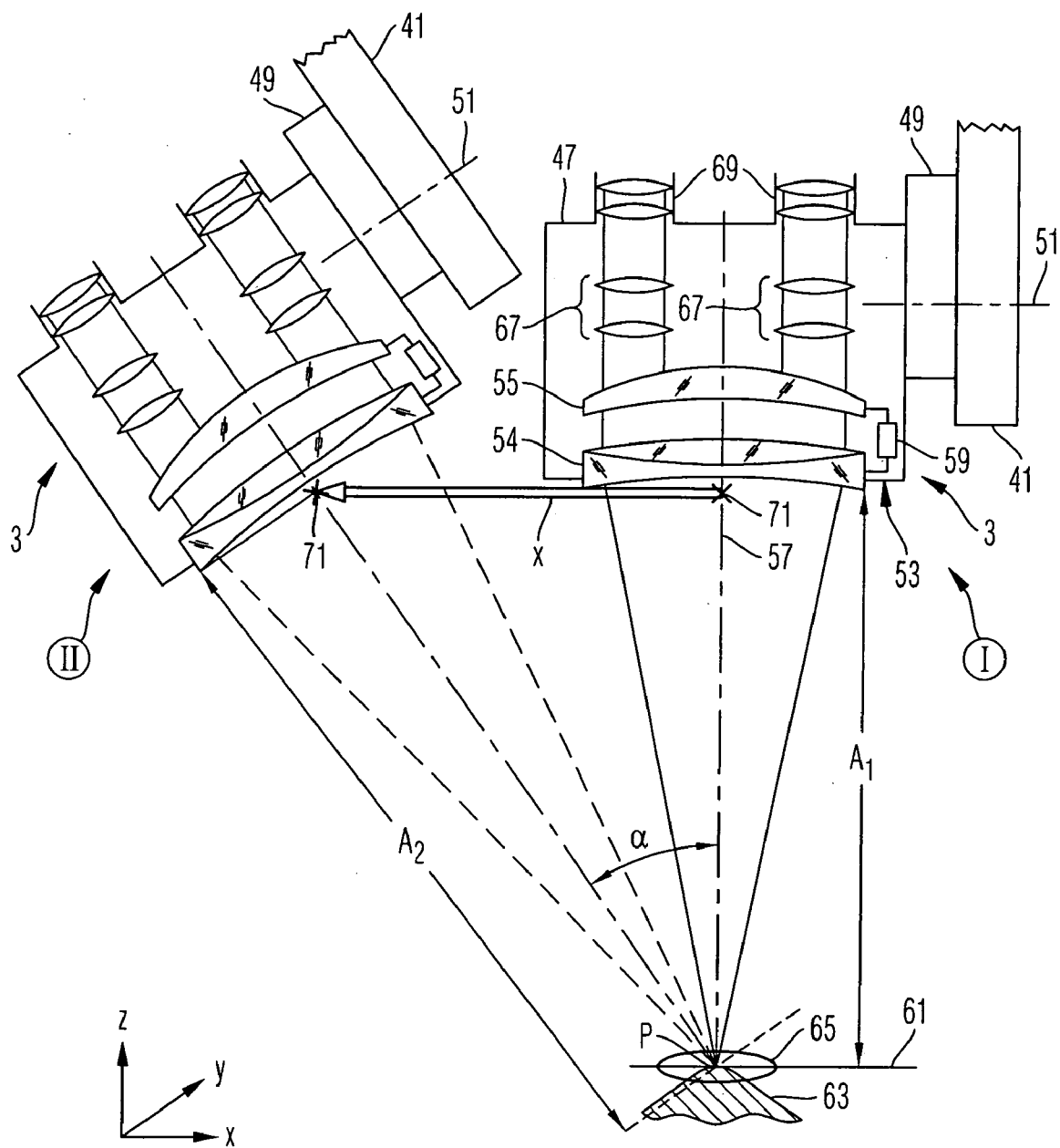
FIG. 2 is a schematic illustration of the microscopy optics of the microscopy system shown in FIG. 1 in two different positions.

In FIG. 2, the microscope 3 is shown in two different positions, namely in a position I on the right hand side and in a position II on a left hand side, whereby only stand member 41 of the stand 5 is shown.

The microscope 3 comprises a microscopy optics having an objective lens 53 which comprises two lens groups 54 and 55 which are displaceable via an actuator 59 along an optical axis 57 in order to adjust a working distance A between the lens group 54 and an object plane 61 such that the object plane coincides with a part of a surface of an object 63 to be observed. A focus region 65 which comprises a part of the object 63 is imaged by the objective lens 53 and the image is supplied to a pair of zoom systems 67 which further supply the image to a pair of oculars 69. The user of the microscopy system 1 looks with both of his eyes into the oculars in order to perceive an enlarged stereoscopic representation or image of the object 63 being disposed in the focus region 65.

Let it be assumed that the microscopy optics is to be moved from position I into position II. The corresponding movement or displacement of the microscopy optics may be understood as a translational displacement of a location 71, which is disposed on the optical axis 57 at a working distance A from the object plane 61, by a distance X and a further rotational displacement of the microscopy optics by an angle $\alpha$ about the location 71. Further the working distance A is changed from a value $A_1$ in position I to a value $A_2$ in position II. Herein, the translational displacement (X), the rotational displacement ($\alpha$) and the change of the working distance (A) are performed such that the focus region 65 remains at a substantially constant position, namely at a same location at the object 63 to be observed such that the substantially same location of the object 63 can be observed in the positions I and II from different points of view or under different viewing angles.

In FIG. 2, the translational displacement X is oriented parallel to the x-direction of the coordinate system for ease of illustration. This is not limiting however, and the translational displacement X may be oriented in any direction, accordingly.

Figure 3:
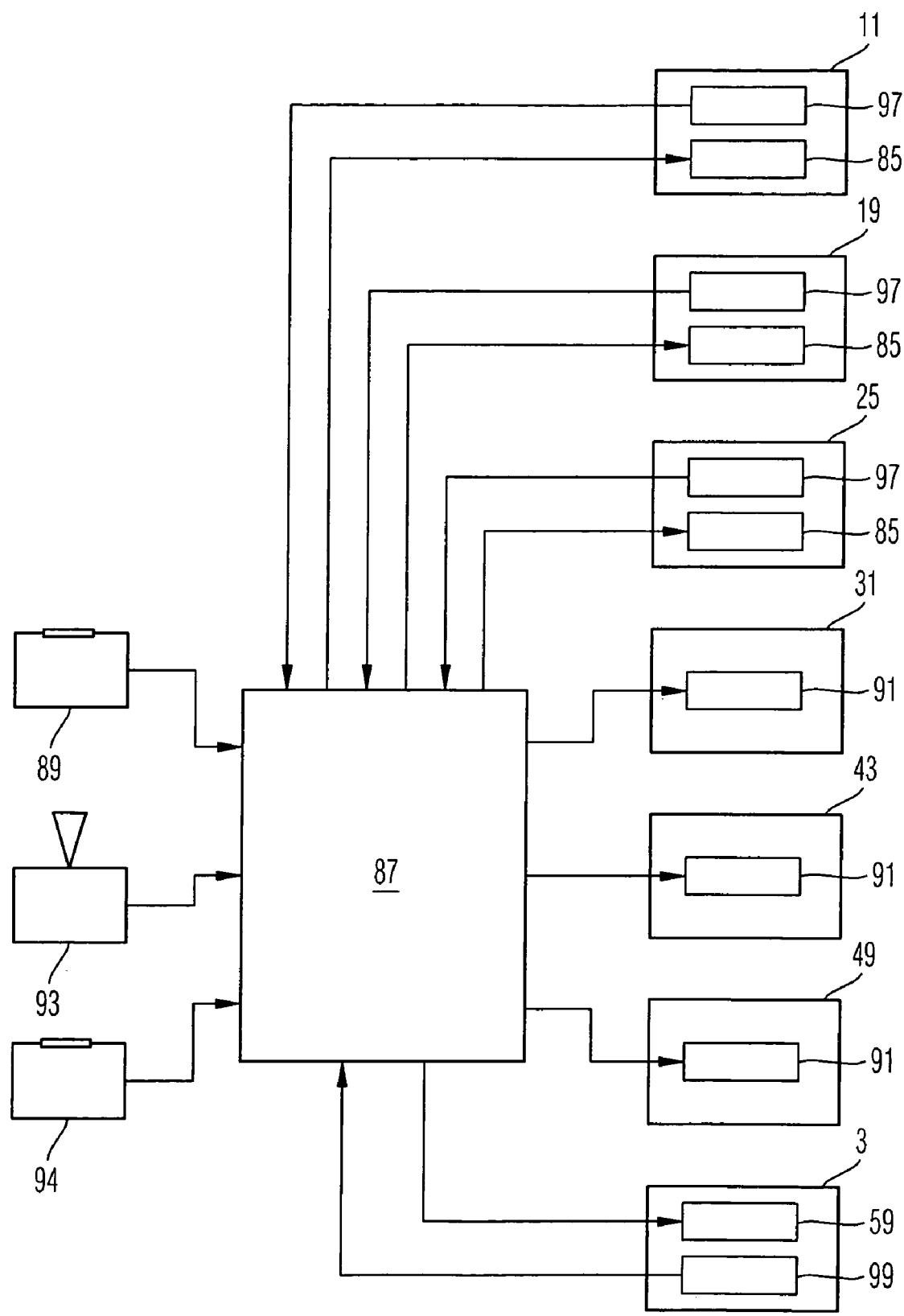
FIG. 3 is a schematic illustration of a controller for controlling the microscopy system shown in FIG. 1.

The arrangement of the microscope 3 in position I and the subsequent displacement into position II will be illustrated with reference to FIG. 3 below.

The hinges 11, 19 and 25 each comprise a brake 85 preventing an accidental displacement of the stand members around the respective axes of the hinges 11, 19 and 25. The brakes 85 are controlled by a controller 87 and are released when the user activates a switch 89. The switch 89 may, for example, be embodied as a mouth switch which is mounted on the microscope chassis 47 in a manner that it can be actuated by the user with his mouth while looking into the oculars 69 with his eyes. An example of a mouth switch is known in the art from U.S. Pat. No. 3,887,267, and the full disclosure of this document is incorporated herein by reference. An actuation of the mouth switch 89 is detected by the controller 87, whereupon the controller 87 controls the brakes 85, such that they release the blocking in the hinges, and the stand members which are connected to each other by the hinges can be displaced about the respective axes with respect to each other. Then, the user can apply a force onto the stand 5 or the microscope chassis 47, in order to displace the microscope 3 near the object 63. The hinges 31, 43 and 49 do not permit free displaceability of the stand members being connected with each other by these hinges. These hinges each have an actuator 91, which is controlled by the controller 87 according to the inputs of the user via a joystick 93 in order to change the orientation of the optical axis 57. By this, the user can move the microscope 3, with respect to location and orientation, into the position I shown in FIG. 2 and observe the desired region of the object 63.

After this, the user actuates a switch 94 in order to switch the controller 87 into an automatic control mode.

In this automatic control mode, the user can actuate switch 89, in order to release the brakes 85 and displace the stand members being connected by the hinges 11, 19 and 25 with respect to each other. Further, the controller 87 obtains measuring values of angle sensors 97, which are comprised in the hinges 11, 19 and 25 respectively, in order to detect the positions of the stand members which are connected with each other by the hinges 11, 19 and 25 relative to each other.

Then, the controller 87 controls the actuators 91 of the hinges 31, 43 and 49 in dependence of the detected changes in positions with an goal that a point P of intersection of the object plane 61 and the optical axis 57 remains as far as possible at a same position. In order to achieve this as far as possible, also the actuator 59 is controlled by the controller 87 in order to change the working distance A of the objective lens 3.

Thus, after actuating the switch 89, the user can displace the microscope 3 by applying a force onto microscope 3 or the stand 5, wherein the hinges 31, 43 and 49 being provided with actuators 91 can be controlled automatically, in order to maintain the focus region 65 at a substantially same position of the object 63.

The automatic control mode of the controller 87 can again be switched off by actuating the switch 94 or by actuating the joystick 93.

According to another exemplary embodiment, all or some of the hinges 31, 43 and 49 being provided with actuators 91 each comprise a brake, which inhibits an accidental displacing of the respective hinges. This alternative is especially selected when the actuators 91 have a gear which is not self-inhibiting. By this, the user can displace the hinges after releasing the brakes either by actuating the actuators 91 or by applying a force onto members of the stand 5, by displacing the respective hinges against the force of the actuators 91. For this, the actuators 91 advantageously can have a slipper clutch or similar.

According to another exemplary embodiment, also the hinges 31, 43 and 49 may comprise angle sensors in order to detect positions of the respective hinges with respect to each other and to transfer the position information to the controller 87. By this, a more exact determination of the displacement of the microscopy optics (distance X in FIG. 2) is possible.

According to a further embodiment, the change of the working distance via actuator 59 is achieved not in dependence of the position data being detected by the angle sensors 97, but in dependence of a distance measurement result, which is supplied to the controller by a distance sensor 99 (FIG. 3) being integrated into microscope 3, in order to form an auto-focus system. An example of an auto-focus system is illustrated in U.S. Pat. No. 4,516,840, the full disclosure of which is incorporated herein by reference.

In the above illustrated embodiment, the controller tries as far as possible to maintain the point of intersection P of object plane 61 and optical axis 57 at the very location in space where the point P has been arranged when switching on the automatic control mode. Alternatively, however, there are also other possibilities. For example, coordinates of the point P, which the controller tries as far as possible to maintain at a same location, can be supplied to the microscopy system via an input interface. The input interface may be provided in the form of a keyboard or a mouse or by an interface to a surgery planning and navigation system, which for example is supplied with physical examination data of a preceding NMR exposure or similar of the patient to be operated. Then, the user can, after visualization of these data, select a point therein, which will be transferred to the controller 87 via the interface, such that the controller, when switching to the automatic control mode, tries to maintain the point of intersection of object plane 61 and optical axis 57 as near as possible close to this point being supplied from external.

Further, a surgery at the brain of a patient is an example where the point P which is maintained at substantially a same location does advantageously not coincide with the focus region 65. The surgery is performed through an opening or channel of the cranium, and it is advantageous to have the point P disposed near the opening of the cranium.

In the embodiment described above, a change of the position of the objective lens is detected by the position detecting sensors which are provided in the hinges 11, 19 and 25. Alternatively, the change of the position may also be determined, for example, by a position detecting system being independent of the hinges of the stand. For example, the position detecting system may detect the position of the objective lens and transfer the coordinates of this position in an appropriate form to the controller 87. Such a position detection system can also be realized, for example, by applying a mark to the chassis 47 of the microscope 3, which is observed, for example, by a plurality of cameras. The position can also be determined by a triangulation method.

Incidentally, the brakes can also be released in another way, for example, by actuating a foot switch or similar being connected to the controller 87 or also by a speech-input means, which senses spoken commands of the user of the microscopy system.

In the above illustrated embodiments, the user perceives the image of the focus region generated by the microscope by looking into the oculars. According to other embodiments of the invention, the microscope comprises a camera detecting a image of the focus region generated by the objective lens, and a display for displaying the detected image for the user. The display may comprise a screen, a head mounted display or other types of displays.

In summary, the invention suggests a microscopy system which comprises a microscopy optics and a stand supporting the microscopy optics. The stand has a plurality of hinges, of which a first group comprises a position detecting sensor for sensing a hinge position and a second group comprising an actuator for the change of the hinge position. In an automatic control mode, the actuators are controlled in dependence of signals of the position detecting sensors.

While the invention has been described also with respect to certain specific embodiments thereof, it is evident that many alternatives, modifications and variations will be apparent to those skilled in the art. Accordingly, the exemplary embodiments of the invention set forth herein are intended to be illustrative and not limiting in any way. Various changes may be made without departing from the spirit and scope of the present invention as defined in the following claims.

The invention claimed is:

1. A microscopy system for displaying an image of an object to be examined, the system comprising:
    a microscopy optics for imaging the object, the microscopy optics comprising at least one objective lens having an optical axis, an object plane and a focus region in which the object to be imaged is to be disposed, wherein the optical axis intersects with the object plane within the focus region; and
    a stand comprising a plurality of stand members, a first hinge group having at least one first hinge and a second hinge group having at least one second hinge, each hinge of the first and second hinge groups connecting a pair of stand members such that the stand members connected by the respective hinge may be displaced relative to each other, the plurality of stand members comprising a base stand member and an objective lens supporting stand member supporting the at least one objective lens;
    the at least one first hinge of the first hinge group allowing, in at least a first mode of operation of the microscopy system, a user to freely displace relative to each other the two stand members hinged together by the first hinge by applying a force to the stand;
    the at least one second-hinge of the second hinge group comprising a first actuator for displacing relative to each other the two stand members hinged together by the second hinge;
    the system further comprising:
    a position detecting system having at least one sensor, wherein the position detecting system is configured to generate a position signal representing a change of a position of the at least one objective lens based on a sensor signal of the at least one sensor; and
    a controller, configured to actuate, in the first mode of operation of the microscopy system, the first actuator of the at least one second hinge to displace the pair of stand members connected by the at least one second hinge based upon the position signal generated by the position detecting system.

2. The microscopy system according to claim 1, wherein the at least one position sensor comprises an angular sensor comprised by the at least one first hinge of the first hinge group.

3. The microscopy system according to claim 1, wherein, in the first operation mode, the at least one objective lens is displaceable relative to a coordinate system which is fixed relative to the base stand member by displacing relative to each other the stand members hinged together by the at least one first hinge of the first hinge group, and
    wherein the controller is further configured to actuate the first actuator of the at least one second hinge to displace the pair of stand members connected by the at least one second hinge such that a displacement of the focus region within the coordinate system is less than a corresponding displacement of the microscopy optics in the coordinate system.

4. The microscopy system according to claim 3, wherein the displacement of the focus region in the coordinate system is less than at least one of 30%, 20%, 10% and 5% of the displacement of the corresponding at least one objective lens in the coordinate system.

5. The microscopy system according to claim 3, wherein the microscopy optics comprises a second actuator for changing a working distance between the at least one objective lens and the object plane, and
    wherein the controller is further configured to actuate, in the first mode of operation, the second actuator of the microscopy optics based upon the position signal generated by the position detecting system.

6. The microscopy system according to claim 1, wherein the first actuator is controllable by the user.

7. The microscopy system according to claim 6, further comprising at least one switch being operable by the user for controlling the first actuator.

8. The microscopy system according to claim 1, wherein at least one first hinge of the first hinge group comprises a brake which is configured to block, in a second mode of operation different from the first mode of operation, the relative displacement of the stand members connected with each other by the at least one first hinge of the first hinge group, and to release, in the first mode of operation, the relative displacement of the stand members connected with each other by the at least one first hinge of the first hinge group.

9. The microscopy system according to claim 8, further comprising a mouth switch being operable by a mouth of the user and being attached to the at least one objective lens for switching the microscopy system from the first mode of operation into the second mode of operation.

* * * * *